(12) United States Patent
Prisco et al.

(10) Patent No.: US 10,376,302 B2
(45) Date of Patent: *Aug. 13, 2019

(54) ROTATING ELECTRICAL CONNECTOR FOR RF ENERGY ENABLED TISSUE DEBRIDEMENT DEVICE

(71) Applicant: Medtronic Xomed, Inc., Jacksonville, FL (US)

(72) Inventors: John R. Prisco, Jacksonville, FL (US); Eric P. Detmers, Jacksonville, FL (US); Wenjeng Li, Saint Johns, FL (US); David J. Little, Ponte Vedra Beach, FL (US); Patrick Richart, Jacksonville, FL (US); Jose Valdez, Jacksonville, FL (US)

(73) Assignee: Medtronic Xomed, Inc., Jacksonville, FL (US)

(*) Notice: Subject to any disclaimer, the term of this patent is extended or adjusted under 35 U.S.C. 154(b) by 374 days.

This patent is subject to a terminal disclaimer.

(21) Appl. No.: 15/046,853

(22) Filed: Feb. 18, 2016

(65) Prior Publication Data

US 2016/0235468 A1 Aug. 18, 2016

Related U.S. Application Data

(60) Provisional application No. 62/117,513, filed on Feb. 18, 2015.

(51) Int. Cl.
*A61B 18/14* (2006.01)
*A61B 18/12* (2006.01)
(Continued)

(52) U.S. Cl.
CPC ........ *A61B 18/14* (2013.01); *A61B 17/32002* (2013.01); *A61B 18/1206* (2013.01);
(Continued)

(58) Field of Classification Search
CPC ... A61B 18/14; A61B 18/1402; A61B 18/148; A61B 18/1482; A61B 18/1485;
(Continued)

(56) References Cited

U.S. PATENT DOCUMENTS 2,888,928 A 6/1959 Seiger
3,191,084 A * 6/1965 Ooka .................. H02K 13/006
310/219

(Continued)

FOREIGN PATENT DOCUMENTS

EP 1201196 5/2002
EP 1853187 11/2007
(Continued)

OTHER PUBLICATIONS

International Search Report and Written Opinion dated May 3, 2016 for International Application No. PCT/US2016/018486 (12 pages).

(Continued)

*Primary Examiner* — Daniel W Fowler
*Assistant Examiner* — Katherine E Maziarski
(74) *Attorney, Agent, or Firm* — Dicke, Billig & Czaja, PLLC (57) ABSTRACT

A bipolar electrosurgical device is disclosed that operates in a mechanical cutting mode and a hemostasis mode. The device includes a housing and a blade assembly extending from the housing. The blade assembly forms a cutting tip and cutting window at a distal end region to provide mechanical cutting of tissue and first and second electrode assemblies to provide electrical energy to tissue. The first and second electrode assemblies can each include a rotary connection assembly to allow spatial orientation of the cutting window relative to the housing and/or cutting tip.

23 Claims, 8 Drawing Sheets

(51) Int. Cl.
*A61B 17/32* (2006.01)
*A61B 18/00* (2006.01)

(52) U.S. Cl.
CPC .............. *A61B 2018/0063* (2013.01); *A61B 2018/00178* (2013.01); *A61B 2018/00208* (2013.01); *A61B 2018/00589* (2013.01); *A61B 2018/00595* (2013.01); *A61B 2018/00601* (2013.01); *A61B 2018/126* (2013.01); *A61B 2018/142* (2013.01); *A61B 2018/1452* (2013.01); *A61B 2218/002* (2013.01); *A61B 2218/007* (2013.01)

(58) Field of Classification Search
CPC ...... A61B 18/1492; A61B 2018/00178; A61B 2018/00202; A61B 2018/00208; A61B 2018/00589; A61B 2018/00595; A61B 2018/0063; A61B 2018/1405; A61B 2018/1472; A61B 2218/002; A61B 2218/007; A61B 17/32; A61B 17/32002; A61B 17/3207; A61B 17/320758; A61B 17/320783; A61B 2017/320024; A61B 2017/320028; A61B 2217/007; A61B 2018/1487; A61B 2017/00446; H04R 39/00; H04R 39/64; H01R 24/38; H01R 24/40; H01R 2201/12; A61N 1/05–1/06
See application file for complete search history.

(56) References Cited

U.S. PATENT DOCUMENTS

| | | |
|---|---|---|
| 3,223,088 A | 12/1965 | Barber et al. |
| 3,682,130 A | 8/1972 | Jeffers |
| 3,750,650 A | 8/1973 | Ruttgers |
| 3,886,944 A | 6/1975 | Jamshidi |
| 3,955,284 A | 5/1976 | Balson |
| 3,955,578 A | 5/1976 | Chamness |
| 4,014,342 A | 3/1977 | Staub |
| 4,060,088 A | 11/1977 | Morrison |
| 4,174,713 A | 11/1979 | Mehl |
| 4,195,637 A | 4/1980 | Gruntzig |
| 4,207,897 A | 6/1980 | Lloyd |
| 4,248,224 A | 2/1981 | Jones |
| 4,651,734 A | 3/1987 | Doss |
| 4,823,791 A * | 4/1989 | D'Amelio ............... A61B 18/14 219/234 |
| 4,878,493 A | 11/1989 | Pasternak |
| 4,931,047 A | 6/1990 | Broadwin et al. |
| 4,932,952 A | 6/1990 | Wojciechowicz |
| 4,943,290 A | 7/1990 | Rexroth |
| 4,950,232 A | 8/1990 | Ruzicka |
| 4,985,030 A | 1/1991 | Melzer |
| 4,998,933 A | 3/1991 | Eggers |
| 5,112,299 A | 5/1992 | Pascaloff |
| 5,190,541 A | 3/1993 | Abele |
| 5,195,959 A | 3/1993 | Smith |
| 5,230,704 A | 7/1993 | Moberg |
| 5,234,428 A | 8/1993 | Kaufman |
| 5,254,117 A | 10/1993 | Rigby |
| 5,275,609 A | 1/1994 | Pingleton |
| 5,281,215 A | 1/1994 | Milder |
| 5,282,799 A | 2/1994 | Rydell |
| 5,330,521 A | 7/1994 | Cohen |
| 5,334,181 A | 8/1994 | Rubinsky |
| 5,336,220 A | 8/1994 | Ryan |
| 5,336,443 A | 8/1994 | Odashima |
| 5,352,222 A | 10/1994 | Rydell |
| 5,364,395 A | 11/1994 | West |
| 5,376,078 A | 12/1994 | Dinger |
| 5,383,874 A | 1/1995 | Jackson |
| 5,385,148 A | 1/1995 | Lesh |
| 5,395,312 A | 3/1995 | Desai |
| 5,401,272 A | 3/1995 | Perkins |
| 5,405,348 A | 4/1995 | Anspach |
| 5,405,376 A | 4/1995 | Mulier |
| 5,413,556 A | 5/1995 | Whittingham |
| 5,417,709 A | 5/1995 | Slater |
| 5,431,168 A | 7/1995 | Webster |
| 5,431,649 A | 7/1995 | Mulier |
| 5,441,503 A | 8/1995 | Considine |
| 5,443,463 A | 8/1995 | Stern |
| 5,445,638 A | 8/1995 | Rydell |
| 5,460,629 A | 10/1995 | Shlain |
| 5,490,819 A | 2/1996 | Nicholas |
| 5,492,527 A | 2/1996 | Glowa |
| 5,496,271 A | 3/1996 | Burton |
| 5,505,700 A | 4/1996 | Leone |
| 5,540,562 A | 7/1996 | Giter |
| 5,540,708 A | 7/1996 | Lim |
| 5,542,196 A | 8/1996 | Kantro |
| 5,542,945 A | 8/1996 | Fritzsch |
| 5,556,397 A | 9/1996 | Long |
| 5,560,373 A | 10/1996 | De Santis |
| 5,562,702 A | 10/1996 | Huitema |
| 5,569,243 A | 10/1996 | Kortenbach |
| 5,569,254 A | 10/1996 | Carlson |
| 5,573,424 A | 11/1996 | Poppe |
| 5,595,183 A | 1/1997 | Swanson |
| 5,599,346 A | 2/1997 | Edwards |
| 5,605,539 A | 2/1997 | Buelna |
| 5,609,573 A | 3/1997 | Sandock |
| 5,620,415 A | 4/1997 | Lucey |
| 5,620,447 A | 4/1997 | Smith |
| 5,647,869 A | 7/1997 | Goble |
| 5,676,693 A | 10/1997 | LaFontaine |
| 5,685,838 A | 11/1997 | Peters |
| 5,688,267 A | 11/1997 | Panescu |
| 5,697,536 A | 12/1997 | Eggers |
| 5,712,543 A | 1/1998 | Sjostrom |
| 5,713,942 A | 2/1998 | Stern |
| 5,733,280 A | 3/1998 | Avitall |
| 5,743,903 A | 4/1998 | Stern |
| 5,766,167 A | 6/1998 | Eggers |
| 5,792,167 A | 8/1998 | Kablik |
| 5,797,905 A | 8/1998 | Fleischman |
| 5,797,960 A | 8/1998 | Stevens |
| 5,810,764 A | 9/1998 | Eggers |
| 5,810,802 A | 9/1998 | Panescu |
| 5,810,809 A | 9/1998 | Rydell |
| 5,814,044 A | 9/1998 | Hooven |
| 5,827,216 A | 10/1998 | Igo |
| 5,836,947 A | 11/1998 | Fleischman |
| 5,840,030 A | 11/1998 | Ferek Petric |
| 5,843,021 A | 12/1998 | Edwards |
| 5,843,152 A | 12/1998 | Tu |
| 5,849,023 A | 12/1998 | Mericle |
| 5,873,855 A | 2/1999 | Eggers |
| 5,873,886 A | 2/1999 | Larsen |
| 5,891,142 A | 4/1999 | Eggers |
| 5,895,355 A | 4/1999 | Schaer |
| 5,897,553 A | 4/1999 | Mulier |
| 5,899,915 A | 5/1999 | Saadat |
| 5,902,272 A | 5/1999 | Eggers et al. |
| 5,904,681 A | 5/1999 | West, Jr. |
| 5,913,854 A | 6/1999 | Maguire |
| 5,916,150 A | 6/1999 | Sillman |
| 5,916,213 A | 6/1999 | Haissaguerre |
| 5,921,982 A | 7/1999 | Lesh |
| 5,925,045 A | 7/1999 | Reimels |
| 5,927,284 A | 7/1999 | Borst |
| 5,928,191 A | 7/1999 | Houser |
| 5,935,123 A | 8/1999 | Edwards |
| 5,941,876 A | 8/1999 | Nardella |
| 5,944,715 A | 8/1999 | Goble |
| 5,957,881 A | 9/1999 | Peters |
| 5,957,919 A | 9/1999 | Laufer |
| 5,971,980 A | 10/1999 | Sherman |
| 5,971,983 A | 10/1999 | Lesh |
| 5,980,516 A | 11/1999 | Mulier |
| 5,989,248 A | 11/1999 | Tu |
| 5,993,412 A | 11/1999 | Deily |
| 6,004,316 A | 12/1999 | Laufer |

(56) References Cited

U.S. PATENT DOCUMENTS

| | | | |
|---|---|---|---|
| 6,004,319 A | 12/1999 | Goble |
| 6,010,476 A | 1/2000 | Saadat |
| 6,010,500 A | 1/2000 | Sherman |
| 6,012,457 A | 1/2000 | Lesh |
| 6,015,391 A | 1/2000 | Rishton |
| 6,024,733 A | 2/2000 | Eggers |
| 6,042,556 A | 3/2000 | Beach |
| 6,042,593 A | 3/2000 | Storz |
| 6,053,923 A | 4/2000 | Veca |
| 6,063,081 A | 5/2000 | Mulier |
| 6,071,279 A | 6/2000 | Whayne |
| 6,074,386 A | 6/2000 | Goble |
| 6,088,894 A | 7/2000 | Oakley |
| 6,096,037 A | 8/2000 | Mulier |
| 6,117,101 A | 9/2000 | Diederich |
| 6,142,993 A | 11/2000 | Whayne |
| 6,142,994 A | 11/2000 | Swanson |
| 6,152,920 A | 11/2000 | Thompson |
| 6,152,941 A | 11/2000 | Himes |
| 6,161,543 A | 12/2000 | Cox |
| 6,165,174 A | 12/2000 | Jacobs |
| 6,193,715 B1 | 2/2001 | Wrublewski |
| 6,197,024 B1 | 3/2001 | Sullivan |
| 6,214,003 B1 | 4/2001 | Morgan |
| 6,217,528 B1 | 4/2001 | Koblish |
| 6,217,576 B1 | 4/2001 | Tu |
| 6,217,598 B1 | 4/2001 | Berman |
| 6,221,088 B1 | 4/2001 | Bays |
| 6,224,592 B1 | 5/2001 | Eggers |
| 6,231,518 B1 | 5/2001 | Grabek |
| 6,235,024 B1 | 5/2001 | Tu |
| 6,237,605 B1 | 5/2001 | Vaska |
| 6,238,347 B1 | 5/2001 | Nix |
| 6,238,393 B1 | 5/2001 | Mulier |
| 6,245,061 B1 | 6/2001 | Panescu |
| 6,245,064 B1 | 6/2001 | Lesh |
| 6,245,065 B1 | 6/2001 | Panescu |
| 6,246,638 B1 | 6/2001 | Zook |
| 6,251,092 B1 | 6/2001 | Qin |
| 6,251,128 B1 | 6/2001 | Knopp |
| 6,270,471 B1 | 8/2001 | Hechel |
| 6,292,689 B1 | 9/2001 | Wallace |
| 6,293,943 B1 | 9/2001 | Panescu |
| 6,293,957 B1 | 9/2001 | Peters |
| 6,296,638 B1 | 10/2001 | Davison |
| 6,325,797 B1 | 12/2001 | Stewart |
| 6,328,736 B1 | 12/2001 | Mulier |
| 6,332,881 B1 | 12/2001 | Carner |
| 6,358,248 B1 | 3/2002 | Mulier |
| 6,361,531 B1 | 3/2002 | Hissong |
| 6,364,876 B1 | 4/2002 | Erb |
| 6,368,275 B1 | 4/2002 | Sliwa |
| 6,383,151 B1 | 5/2002 | Diederich |
| 6,385,472 B1 | 5/2002 | Hall |
| 6,398,792 B1 | 6/2002 | O'Connor |
| 6,409,722 B1 | 6/2002 | Hoey |
| 6,413,254 B1 | 7/2002 | Hissong |
| 6,419,648 B1 | 7/2002 | Vitek |
| 6,425,867 B1 | 7/2002 | Vaezy |
| 6,430,426 B2 | 8/2002 | Avitall |
| 6,440,130 B1 | 8/2002 | Mulier |
| 6,443,952 B1 | 9/2002 | Mulier |
| 6,454,782 B1 | 9/2002 | Schwemberger |
| 6,461,357 B1 | 10/2002 | Sharkey |
| 6,471,697 B1 | 10/2002 | Lesh |
| 6,471,698 B1 | 10/2002 | Edwards |
| 6,474,340 B1 | 11/2002 | Vaska |
| 6,475,216 B2 | 11/2002 | Mulier |
| 6,477,396 B1 | 11/2002 | Mest |
| 6,484,727 B1 | 11/2002 | Vaska |
| 6,488,678 B2 | 12/2002 | Sherman |
| 6,488,680 B1 | 12/2002 | Francischelli |
| 6,494,892 B1 | 12/2002 | Ireland |
| 6,502,575 B1 | 1/2003 | Jacobs |
| 6,503,263 B2 | 1/2003 | Adams |
| 6,514,250 B1 | 2/2003 | Jahns |
| 6,527,767 B2 | 3/2003 | Wang |
| 6,537,248 B2 | 3/2003 | Mulier |
| 6,537,272 B2 | 3/2003 | Christopherson |
| 6,558,382 B2 | 5/2003 | Jahns |
| 6,558,385 B1 | 5/2003 | McClurken |
| 6,565,560 B1 | 5/2003 | Goble |
| 6,565,561 B1 | 5/2003 | Goble |
| 6,584,360 B2 | 6/2003 | Francischelli |
| 6,585,732 B2 | 7/2003 | Mulier |
| 6,605,084 B2 | 8/2003 | Acker |
| 6,610,055 B1 | 8/2003 | Swanson |
| 6,610,059 B1 | 8/2003 | West, Jr. |
| 6,610,060 B2 | 8/2003 | Mulier |
| 6,613,048 B2 | 9/2003 | Mulier |
| 6,623,500 B1 * | 9/2003 | Cook ............ A61B 17/320068 606/170 |
| 6,645,199 B1 | 11/2003 | Jenkins |
| 6,648,883 B2 | 11/2003 | Francischelli |
| 6,656,175 B2 | 12/2003 | Francischelli |
| 6,663,627 B2 | 12/2003 | Francischelli |
| 6,663,628 B2 | 12/2003 | Peters |
| 6,689,131 B2 | 2/2004 | McClurken |
| 6,699,240 B2 | 3/2004 | Francischelli |
| 6,702,810 B2 | 3/2004 | McClurken |
| 6,702,811 B2 | 3/2004 | Stewart |
| 6,706,038 B2 | 3/2004 | Francischelli |
| 6,706,039 B2 | 3/2004 | Mulier |
| 6,716,211 B2 | 4/2004 | Mulier |
| 6,716,215 B1 | 4/2004 | David |
| 6,736,810 B2 | 5/2004 | Hoey |
| 6,752,816 B2 | 6/2004 | Culp |
| 6,755,827 B2 | 6/2004 | Mulier |
| 6,764,487 B2 | 7/2004 | Mulier |
| 6,773,433 B2 | 8/2004 | Stewart |
| 6,776,780 B2 | 8/2004 | Mulier |
| 6,780,180 B1 | 8/2004 | Goble |
| 6,807,968 B2 | 10/2004 | Francischelli |
| 6,824,550 B1 | 11/2004 | Noriega |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart |
| 6,911,019 B2 | 6/2005 | Mulier |
| 6,916,318 B2 | 7/2005 | Francischelli |
| 6,923,803 B2 | 8/2005 | Goble |
| 6,936,046 B2 | 8/2005 | Hissong |
| 6,949,097 B2 | 9/2005 | Stewart |
| 6,949,098 B2 | 9/2005 | Mulier |
| 6,953,461 B2 | 10/2005 | McClurken |
| 6,960,205 B2 | 11/2005 | Jahns |
| 6,962,589 B2 | 11/2005 | Mulier |
| 6,979,332 B2 | 12/2005 | Adams |
| 7,052,494 B2 | 5/2006 | Goble |
| 7,115,139 B2 | 10/2006 | McClurken |
| 7,150,747 B1 | 12/2006 | McDonald |
| 7,166,103 B2 | 1/2007 | Carmel |
| 7,179,255 B2 | 2/2007 | Lettice |
| 7,229,437 B2 | 6/2007 | Johnson |
| 7,232,440 B2 | 6/2007 | Dumbauld |
| 7,237,990 B2 | 7/2007 | Deng |
| 7,247,155 B2 | 7/2007 | Hoey |
| 7,247,161 B2 | 7/2007 | Johnston |
| 7,261,711 B2 | 8/2007 | Mulier |
| 7,276,074 B2 | 10/2007 | Adams |
| 7,278,994 B2 | 10/2007 | Goble |
| 7,309,325 B2 | 12/2007 | Mulier |
| 7,311,708 B2 | 12/2007 | McClurken |
| 7,322,974 B2 | 1/2008 | Swoyer |
| 7,361,175 B2 | 4/2008 | Suslov |
| 7,364,579 B2 | 4/2008 | Mulier |
| 7,416,539 B2 | 8/2008 | Johnston |
| 7,442,191 B2 | 10/2008 | Hovda |
| 7,537,595 B2 | 5/2009 | McClurken |
| 7,604,635 B2 | 10/2009 | McClurken |
| 7,608,072 B2 | 10/2009 | Swanson |
| 7,645,277 B2 | 1/2010 | McClurken |
| 7,651,494 B2 | 1/2010 | McClurken |

(56) References Cited

U.S. PATENT DOCUMENTS

| | | | |
|---|---|---|---|
| 7,674,263 B2* | 3/2010 | Ryan | A61B 18/148 606/180 |
| 7,691,050 B2 | 4/2010 | Gellman | |
| 7,699,846 B2 | 4/2010 | Ryan | |
| 7,736,361 B2 | 6/2010 | Palanker | |
| 7,749,608 B2 | 7/2010 | Laude | |
| 7,785,337 B2 | 8/2010 | Adams | |
| 7,811,282 B2 | 10/2010 | McClurken | |
| 7,815,634 B2 | 10/2010 | McClurken | |
| 7,854,736 B2 | 12/2010 | Ryan | |
| 7,909,820 B2 | 3/2011 | Lipson | |
| 7,942,872 B2 | 5/2011 | Ein-Gal | |
| 7,976,544 B2 | 7/2011 | McClurken | |
| 7,993,337 B2 | 8/2011 | Lesh | |
| 7,997,278 B2 | 8/2011 | Utley | |
| 7,998,140 B2 | 8/2011 | McClurken | |
| 8,012,153 B2 | 9/2011 | Woloszko | |
| 8,034,071 B2 | 10/2011 | Scribner | |
| 8,038,670 B2 | 10/2011 | McClurken | |
| 8,048,070 B2 | 11/2011 | O'Brien | |
| 8,083,736 B2 | 12/2011 | McClurken | |
| 8,105,323 B2 | 1/2012 | Buysse | |
| 8,109,956 B2 | 2/2012 | Shadeck | |
| 8,172,828 B2 | 5/2012 | Chang | |
| 8,177,783 B2 | 5/2012 | Davison | |
| 8,202,288 B2 | 6/2012 | Adams | |
| 8,216,233 B2 | 7/2012 | McClurken | |
| 8,277,474 B2* | 10/2012 | Norman | A61B 17/32002 606/171 |
| 8,317,786 B2 | 11/2012 | Dahla | |
| 8,323,276 B2 | 12/2012 | Palanker | |
| 8,348,946 B2 | 1/2013 | McClurken | |
| 8,361,068 B2 | 1/2013 | McClurken | |
| 8,377,086 B2 | 2/2013 | Flynn | |
| 8,388,642 B2 | 3/2013 | Muni | |
| 8,414,572 B2 | 4/2013 | Davison | |
| 8,568,419 B2 | 10/2013 | de Wekker | |
| 9,226,792 B2 | 1/2016 | Bloom | |
| 2001/0047183 A1 | 11/2001 | Privitera | |
| 2002/0038129 A1 | 3/2002 | Peters | |
| 2002/0049483 A1 | 4/2002 | Knowlton | |
| 2002/0062131 A1 | 5/2002 | Gallo | |
| 2002/0082643 A1 | 6/2002 | Milla | |
| 2002/0165549 A1 | 11/2002 | Owusu Akyaw | |
| 2003/0014050 A1 | 1/2003 | Sharkey | |
| 2003/0032954 A1 | 2/2003 | Carranza | |
| 2003/0045872 A1 | 3/2003 | Jacobs | |
| 2003/0073993 A1 | 4/2003 | Ciarrocca | |
| 2003/0097129 A1 | 5/2003 | Davison | |
| 2003/0144656 A1 | 7/2003 | Ocel | |
| 2003/0165794 A1 | 9/2003 | Matoba | |
| 2003/0191462 A1 | 10/2003 | Jacobs | |
| 2003/0204185 A1 | 10/2003 | Sherman | |
| 2003/0216724 A1 | 11/2003 | Jahns | |
| 2004/0010258 A1 | 1/2004 | Carusillo | |
| 2004/0015106 A1 | 1/2004 | Coleman | |
| 2004/0015219 A1 | 1/2004 | Francischelli | |
| 2004/0024395 A1 | 2/2004 | Ellman | |
| 2004/0044340 A1 | 3/2004 | Francischelli | |
| 2004/0049179 A1 | 3/2004 | Francischelli | |
| 2004/0078069 A1 | 4/2004 | Francischelli | |
| 2004/0082948 A1 | 4/2004 | Stewart | |
| 2004/0087940 A1 | 5/2004 | Jahns | |
| 2004/0092926 A1 | 5/2004 | Hoey | |
| 2004/0111136 A1 | 6/2004 | Sharkey | |
| 2004/0111137 A1 | 6/2004 | Shankey | |
| 2004/0116923 A1 | 6/2004 | Desinger | |
| 2004/0138621 A1 | 7/2004 | Jahns | |
| 2004/0138656 A1 | 7/2004 | Francischelli | |
| 2004/0143260 A1 | 7/2004 | Francischelli | |
| 2004/0167427 A1 | 8/2004 | Quick | |
| 2004/0186465 A1 | 9/2004 | Francischelli | |
| 2004/0215183 A1 | 10/2004 | Hoey | |
| 2004/0220560 A1 | 11/2004 | Briscoe | |
| 2004/0236322 A1 | 11/2004 | Mulier | |
| 2004/0243163 A1 | 12/2004 | Casiano | |
| 2004/0267326 A1 | 12/2004 | Ocel | |
| 2005/0010095 A1 | 1/2005 | Stewart | |
| 2005/0033280 A1 | 2/2005 | Francischelli | |
| 2005/0090815 A1 | 4/2005 | Francischelli | |
| 2005/0090816 A1 | 4/2005 | McClurken | |
| 2005/0143729 A1 | 6/2005 | Francischelli | |
| 2005/0165392 A1 | 7/2005 | Francischelli | |
| 2005/0171525 A1 | 8/2005 | Rioux | |
| 2005/0209564 A1 | 9/2005 | Bonner | |
| 2005/0222566 A1 | 10/2005 | Nakahira | |
| 2005/0267454 A1 | 12/2005 | Hissong | |
| 2005/0277970 A1 | 12/2005 | Norman | |
| 2006/0009756 A1 | 1/2006 | Francischelli | |
| 2006/0009759 A1 | 1/2006 | Christian | |
| 2006/0064085 A1 | 3/2006 | Schechter | |
| 2006/0106375 A1 | 5/2006 | Werneth | |
| 2006/0200123 A1 | 9/2006 | Ryan | |
| 2006/0259055 A1 | 11/2006 | Thorne | |
| 2007/0049920 A1 | 3/2007 | McClurken | |
| 2007/0093808 A1 | 4/2007 | Mulier | |
| 2007/0100336 A1 | 5/2007 | McFarlin et al. | |
| 2007/0118114 A1 | 5/2007 | Miller | |
| 2007/0149965 A1 | 6/2007 | Gallo | |
| 2007/0179495 A1 | 8/2007 | Mitchell | |
| 2007/0208332 A1 | 9/2007 | Mulier | |
| 2008/0015563 A1 | 1/2008 | Hoey | |
| 2008/0042513 A1* | 2/2008 | Kuenzel | H01R 39/381 310/247 |
| 2008/0058796 A1 | 3/2008 | O'Brien | |
| 2008/0071270 A1 | 3/2008 | Desinger | |
| 2008/0207028 A1 | 8/2008 | Schutz | |
| 2008/0262489 A1 | 10/2008 | Steinke | |
| 2009/0118729 A1 | 5/2009 | Auth | |
| 2009/0264879 A1 | 10/2009 | McClurken | |
| 2009/0270896 A1 | 10/2009 | Sullivan | |
| 2009/0306655 A1 | 12/2009 | Stangenes | |
| 2010/0087812 A1 | 4/2010 | Davison | |
| 2010/0100095 A1 | 4/2010 | McClurken | |
| 2010/0160906 A1 | 6/2010 | Jarrard | |
| 2010/0241178 A1 | 9/2010 | Tilson | |
| 2010/0298763 A1 | 11/2010 | Adams | |
| 2010/0298855 A1 | 11/2010 | Dierck | |
| 2010/0317998 A1 | 12/2010 | Hibner | |
| 2011/0009856 A1 | 1/2011 | Jorgensen | |
| 2011/0017801 A1 | 1/2011 | Zemlok | |
| 2011/0028965 A1 | 2/2011 | McClurken | |
| 2011/0066142 A1 | 3/2011 | Tal | |
| 2011/0137298 A1 | 6/2011 | Nguyen | |
| 2011/0178515 A1 | 7/2011 | Bloom | |
| 2011/0196367 A1 | 8/2011 | Gallo | |
| 2011/0295249 A1 | 12/2011 | Bloom | |
| 2011/0301578 A1 | 12/2011 | Muniz-Medina | |
| 2011/0319889 A1 | 12/2011 | Conley | |
| 2012/0004657 A1 | 1/2012 | Conley | |
| 2012/0012638 A1 | 1/2012 | Huang et al. | |
| 2012/0071712 A1 | 3/2012 | Manwaring | |
| 2012/0101496 A1 | 4/2012 | McClurken | |
| 2012/0109130 A1 | 5/2012 | Casey | |
| 2012/0116261 A1* | 5/2012 | Mumaw | A61B 17/00234 601/2 |
| 2012/0116397 A1 | 5/2012 | Rencher | |
| 2012/0143293 A1 | 6/2012 | Mauch | |
| 2012/0150165 A1 | 6/2012 | Conley | |
| 2012/0157989 A1 | 6/2012 | Stone | |
| 2012/0172877 A1 | 7/2012 | Ryan | |
| 2012/0179158 A1 | 7/2012 | Stierman | |
| 2012/0184983 A1 | 7/2012 | Chang | |
| 2012/0191084 A1 | 7/2012 | Davison | |
| 2012/0191117 A1 | 7/2012 | Palmer | |
| 2012/0215245 A1 | 8/2012 | Palmer | |
| 2012/0221035 A1 | 8/2012 | Harvey | |
| 2012/0253343 A1 | 10/2012 | McClurken | |
| 2012/0330292 A1 | 12/2012 | Shadduck | |
| 2013/0004595 A1 | 1/2013 | Bhatia | |
| 2013/0053830 A1 | 2/2013 | Edwards | |
| 2013/0085498 A1 | 4/2013 | Matusaitis | |
| 2013/0331833 A1* | 12/2013 | Bloom | A61B 18/1445 606/33 |

(56) References Cited

U.S. PATENT DOCUMENTS

| | | | |
|---|---|---|---|
| 2013/0345704 A1* | 12/2013 | Palmer | A61B 18/148 606/46 |
| 2014/0005700 A1 | 1/2014 | Casey | |
| 2014/0100567 A1 | 4/2014 | Edwards | |
| 2014/0132126 A1* | 5/2014 | Vicars | H01R 39/12 310/68 R |
| 2014/0155888 A1 | 6/2014 | Edwards | |
| 2014/0155889 A1 | 6/2014 | Edwards | |
| 2014/0155923 A1 | 6/2014 | Edwards | |
| 2014/0207217 A1* | 7/2014 | Lischinsky | A61N 1/36014 607/102 |
| 2014/0276808 A1 | 9/2014 | Gittard et al. | |
| 2014/0277036 A1 | 9/2014 | Flynn | |
| 2015/0265337 A1 | 9/2015 | Bloom | |
| 2016/0235469 A1 | 8/2016 | Prisco et al. | |
| 2016/0235474 A1 | 8/2016 | Prisco et al. | |
| 2017/0143406 A1 | 5/2017 | Bloom | |

FOREIGN PATENT DOCUMENTS

| | | |
|---|---|---|
| EP | 2044893 | 4/2009 |
| EP | 2133028 | 12/2009 |
| EP | 1853187 | 10/2011 |
| GB | 247060 | 12/2010 |
| WO | WO1996/037156 | 11/1996 |
| WO | WO1997/023169 | 7/1997 |
| WO | WO1998/034550 | 8/1998 |
| WO | WO1998/038932 | 9/1998 |
| WO | WO2003/079911 | 10/2003 |
| WO | WO2011/037664 | 3/2011 |
| WO | WO2012/102838 | 8/2012 |
| WO | 2013191811 | 12/2013 |
| WO | WO2014/084983 | 6/2014 |
| WO | WO2014/133663 | 9/2014 |

OTHER PUBLICATIONS

Non-Final Office Action for U.S. Appl. No. 15/047,242 dated Jul. 10, 2018 (32 pages).

Non-Final Office Action for U.S. Appl. No. 14/951,697 dated Jul. 12, 2018 (40 pages).

Non-Final Office Action for U.S. Appl. No. 15/046,869 dated Mar. 28, 2018 (29 pages).

Non-Final Office Action for U.S. Appl. No. 14/951,697 dated Jan. 23, 2019 (25 pages).

Final Office Action for U.S. Appl. No. 15/047,242 dated Jan. 25, 2019 (20 pages).

Notice of Allowance for U.S. Appl. No. 15/046,869 dated Oct. 9, 2018 (23 pages).

Non-Final Office Action for U.S. Appl. No. 15/047,242 dated Apr. 11, 2019 (28 pages).

* cited by examiner

Fig. 9B

ROTATING ELECTRICAL CONNECTOR FOR RF ENERGY ENABLED TISSUE DEBRIDEMENT DEVICE

CROSS REFERENCE TO RELATED APPLICATIONS

This Non-Provisional Patent Application claims the benefit of the filing date of U.S. Provisional Patent Application Ser. No. 62/117,513, filed Feb. 18, 2015, entitled "ROTATING ELECTRICAL CONNECTOR FOR RF ENERGY ENABLED TISSUE DEBRIDEMENT DEVICE," which is herein incorporated by reference.

BACKGROUND

This disclosure is generally directed to devices, systems and methods for cutting and sealing tissue such as bone and soft tissue. The concepts presented herein may be particularly suitable for sinus applications and nasopharyngeal/laryngeal procedures and may combine or provide Transcollation® technology with a microdebrider device.

Devices, systems and methods according to the present disclosure may be suitable for a variety of procedures including ear, nose and throat (ENT) procedures, head and neck procedures, otology procedures, including otoneurologic procedures. The present disclosure may be suitable for a varient of other surgical procedures including mastoidectomies and mastoidotomies; nasopharyngeal and laryngeal procedures such as tonsillectomies, trachael procedures, adenoidectomies, laryngeal lesion removal, and polypectomies; for sinus procedures such as polypectomies, septoplasties, removals of septal spurs, anstrostomies, frontal sinus trephination and irrigation, frontal sinus opening, endoscopic DCR, correction of deviated septums and trans-sphenoidal procedures; rhinoplasty and removal of fatty tissue in the maxillary and mandibular regions of the face.

Sinus surgery is challenging due to its location to sensitive organs such as the eyes and brain, the relatively small size of the anatomy of interest to the surgeon, and the complexity of the typical procedures. Examples of debriders with mechanical cutting components are described in U.S. Pat. Nos. 5,685,838; 5,957,881 and 6,293,957. These devices are particularly successful for powered tissue cutting and removal during sinus surgery, but do not include any mechanism for sealing tissue to reduce the amount of bleeding from the procedure. Sealing tissue is especially desirable during sinus surgery which tends to be a complex and precision oriented practice.

Current approaches to sealing tissue include utilizing Transcollation® technology, where sealing energy is supplied by the Aquamantys® System (available from Medtronic Advanced Energy of Portsmouth, N.H.), which stops bleeding and reduces blood loss during and after surgery. The technology uses a combination of radiofrequency (RF) energy and saline to provide hemostatic sealing of soft tissue and bone, which may lower transfusion rates and reduce the need for other blood management products during or after surgery. Transcollation® technology integrates RF energy and saline to deliver controlled thermal energy to tissue. Coupling of saline and RF energy allows a device temperature to stay in a range which produces a tissue effect without the associated charring found in other ablation methods.

Other devices include both mechanical cutting as well as cauterization or electrocauterization energy. For example, the PK diego® powered dissector is commercially available from Gyms ENT of Bartlett, Tenn. This device utilizes two mechanical cutting blade components that are moveable relative to each other, one of which acts as an electrode in a bipolar cauterization system. While providing cauterization and cutting, this device limits rotational movement of portions of a distal end of the device. As such, surgeons are forced to rotate a hand piece of the device in particular situations, which can cause injury to patients and/or frustration to surgeons.

SUMMARY

A bipolar electrosurgical device is disclosed that operates in a mechanical cutting mode and a hemostasis mode. The device includes a housing and a blade assembly extending from the housing. The blade assembly forms a cutting tip and cutting window at a distal end region to provide mechanical cutting of tissue and first and second electrode assemblies to provide electrical energy to tissue. The first and second electrode assemblies can each include a rotary connection assembly to allow spatial orientation of the cutting window relative to the housing and/or cutting tip.

DETAILED DESCRIPTION

In one aspect of exemplary concepts discussed herein, a bipolar electrosurgical device includes a rotary electrical connection assembly. The assembly includes an outer connector defining an engagement surface and an inner connector rotatably disposed within the outer connector about a rotational axis. The inner connector includes a first surface in contact with the engagement surface of the outer connector and a second surface opposite the first surface. An extension member extends from the second surface in a direction away from the first surface, the member defining a natural position and a deflected position. An electrode defining an outer arcuate connecting surface is positioned in contact with the extension member such that the extension member is in the deflected position. In further embodiments, the rotary electrode assembly can be included with one or more of a blade assembly extending from a housing, an irrigation path and a handpiece. When utilized with a blade assembly, a spatial orientation of a cutting window can be rotated a full 360 degrees relative to the housing.

Figure 1:
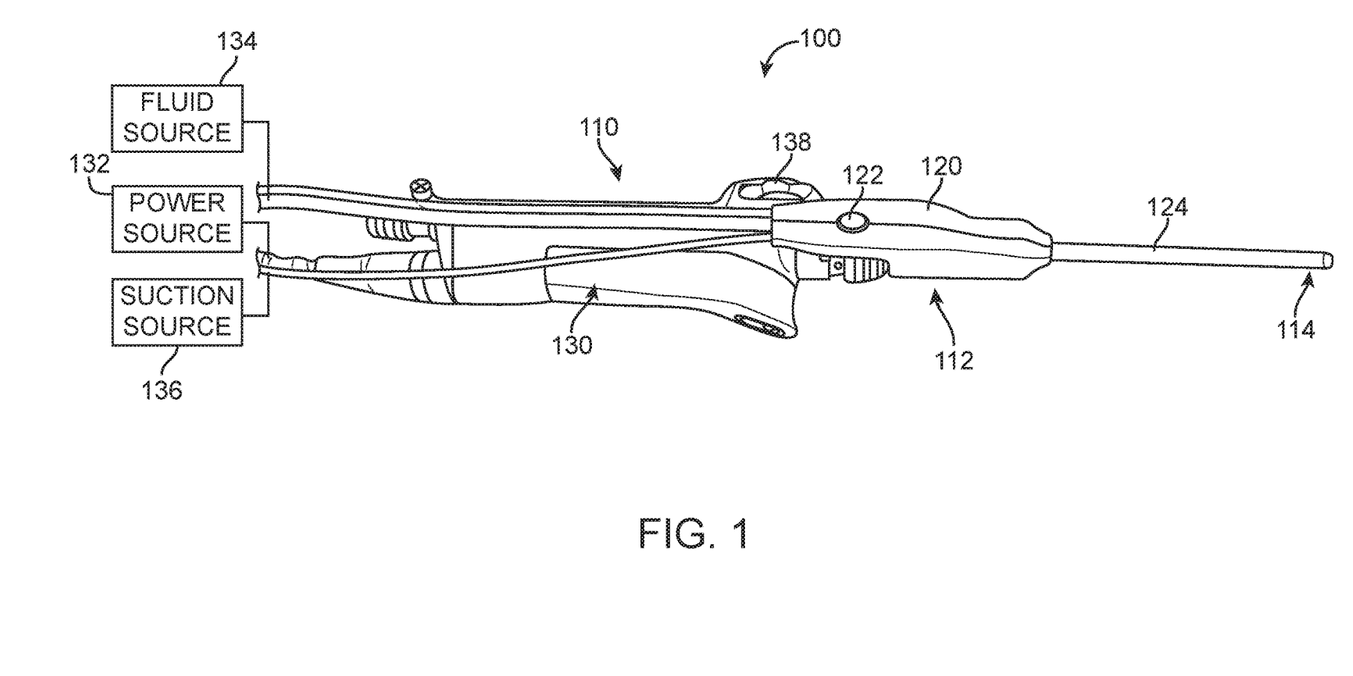
FIG. 1 is a schematic view of a system including a bipolar electrical device.

FIG. 1 illustrates a system 100 that includes a bipolar electrical device 110 having a proximal end region indicated generally at 112 and a distal end region indicated generally at 114. Proximal end region 112 includes a housing 120 maintaining a button 122. A blade assembly 124 extends from the housing to the distal end region 114. As discussed in more detail below, the blade assembly 124 maintains a cutting implement and an electrode assembly to mechanically cut and cauterize or electrocuaterize tissue, respectively.

System 100 further includes a handpiece 130, a power source 132, a fluid source 134 and a suction source 136. It will be appreciated that power source 132, fluid source 134 and suction source 136 can be formed of one or more separate sources as desired and not limited to a single source. Device 110 is configured to couple to handpiece 130, which can be manipulated by a user (e.g., a surgeon) during operation of the system 100 to cut and cauterize or electrocuaterize tissue. In one embodiment, in order to cut tissue, handpiece 130 includes a motor (not shown) internal to the handpiece 130 that is coupled with power source 132. The motor is rotationally coupled with the blade assembly 124 to provide mechanical cutting. The handpiece 130 further includes an actuator 138 external to the handpiece 130 that can be used for manual rotation of one or more components of the device 110 relative to the housing 120 and the handpiece 130. One exemplary handpiece and associated actuator is further described in U.S. Pat. No. 8,277,474, issued Oct. 2, 2012 and entitled "Surgical Cutting Instrument"; the contents of which are hereby incorporated by reference in their entirety.

Power source 132 can further be coupled with the device 110 to deliver electrical energy through blade assembly 124 to the distal region 114. For example, power source 132 can include a generator and optionally may be designed for use with bipolar energy or a bipolar energy supply. For example, the Transcollation® sealing energy supplied by the Aquamantys® System (available from Medtronic Advanced Energy of Portsmouth, N.H.) may be used.

Fluid can be provided to distal region 114 through fluid source 134 connected directly to device 110 and/or to device 110 through handpiece 130. One fluid useful with the present disclosure is saline, however, other fluids are contemplated. Suction source 136 can be coupled to handpiece 130. Use of fluid in conjunction with energy delivery aids in providing optimal tissue effect, thus embodiments of the present disclosure include specific arrangement of the device 110 for coupling of energy with a fluid. In use, a fluid (e.g., saline) may be emitted from an opening at the distal end region 114 of the device 110. Tissue fragments and fluids can be removed from a surgical site through an opening in the distal end region 114 via the suction source 136, as will be further explained below. Both the fluid source 134 and suction source 136 are optional components of system 100.

Figure 2A:
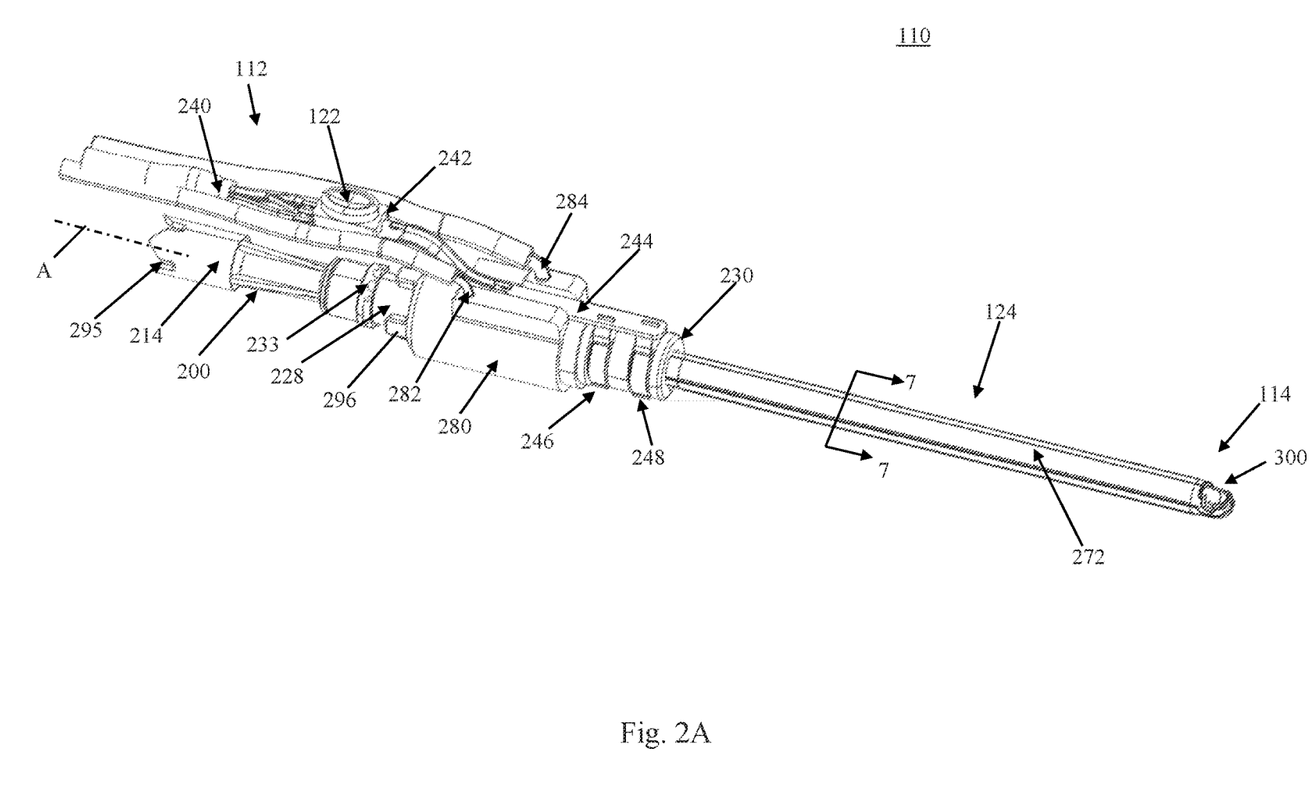
FIG. 2A is an isometric view the bipolar electrical device illustrated in FIG. 1 with a housing removed.
Figure 2B:
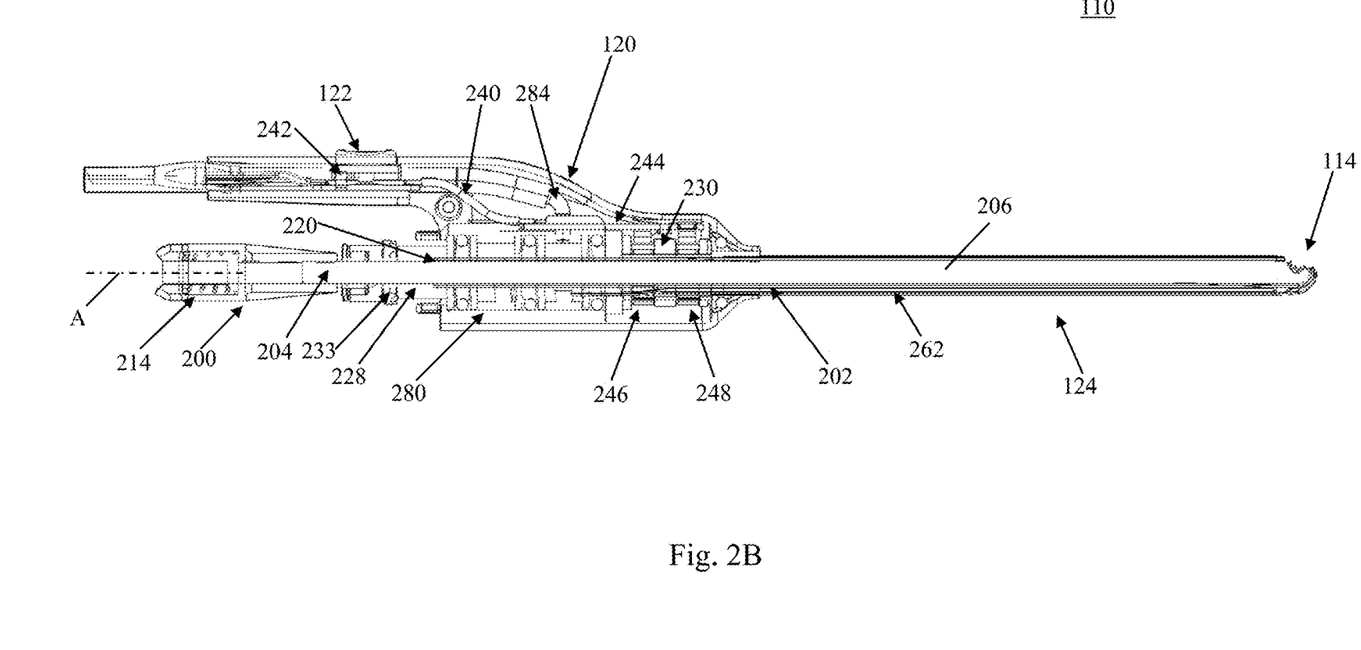
FIG. 2B is a cross sectional view of the bipolar electrical device illustrated in FIG. 1.

With further reference to FIGS. 2A and 2B, an isometric view of device 110 with housing 120 removed and a cross section of device 110 are provided. Details for operation of device 110 are provided below. In general, device 110, and in particular blade assembly 124, includes an inner shaft assembly 200 rotatably disposed within an outer shaft assembly 202. Upon final assembly, the device 110 is operable with the handpiece 130 (FIG. 1) to provide mechanical cutting due to rotation between the inner shaft assembly 200 and the outer shaft assembly 202. Further details of the inner shaft assembly 200 and outer shaft assembly 202 are provided below in relation to FIGS. 3 and 4, respectively. In addition to mechanical cutting, device 110 is operable to provide energy to tissue through a first electrode assembly 246 and a second electrode assembly 248 due to operation of button 122, further described below with respect to FIG. 5. Also during operation, device 110 can provide irrigation through an irrigation path to distal end region 114, for example interior to outer shaft assembly 202 and/or exterior to outer shaft assembly 202, as discussed below with respect to FIGS. 6 and 7.

Figure 8A:
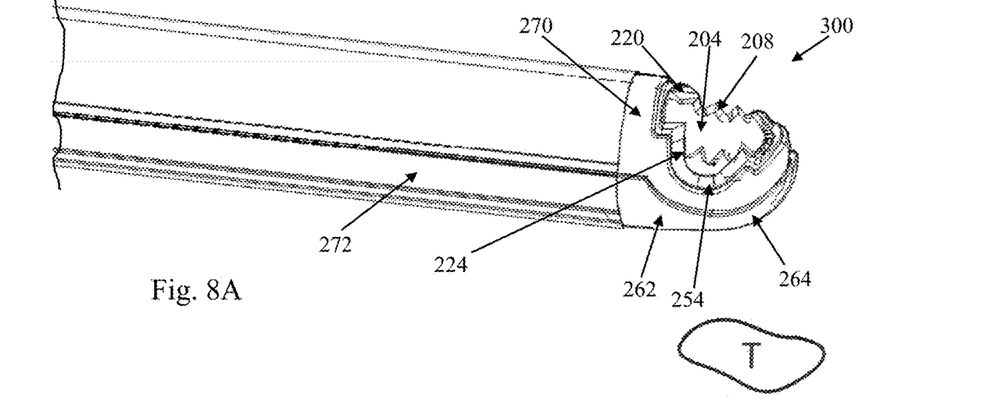
FIGS. 8A and 8B are isometric views of a distal end region of a bipolar electrical device in first and second special orientations, respectively.
Figure 8B:
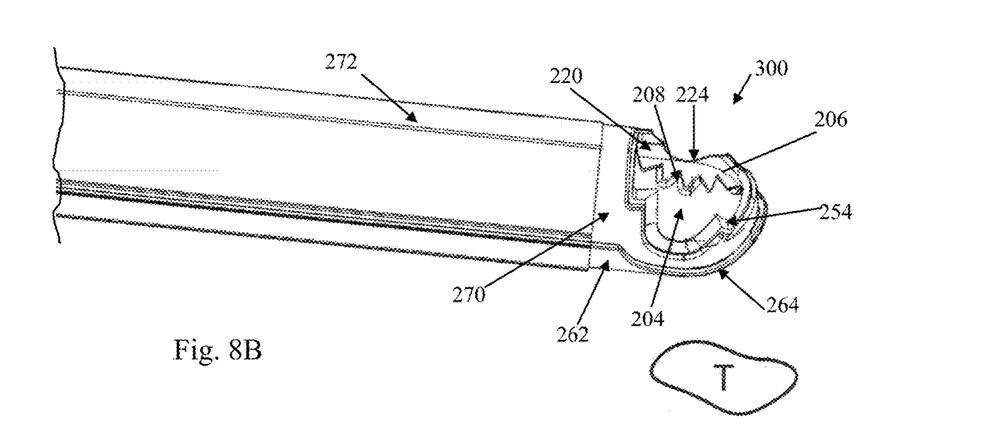

During use, a user, through operation of actuator 138, can rotate the outer shaft assembly 202 with respect to housing 120 and/or inner shaft assembly 200 so as to alter an orientation of the outer shaft assembly 202 with respect to tissue of interest, as further discussed with respect to FIGS. 8A and 8B. In particular, the outer shaft assembly 202 can be rotated a full 360 degrees with respect to the housing 120 and/or inner shaft assembly 200. In order to allow full 360 degree rotation, a suitable rotary electrical connector assembly as discussed with respect to FIGS. 9A and 9B can be utilized. During the full 360 degree rotation, electrical connection with between the electrode assemblies 246, 248 and power source 132 can be maintained.

Figure 3:
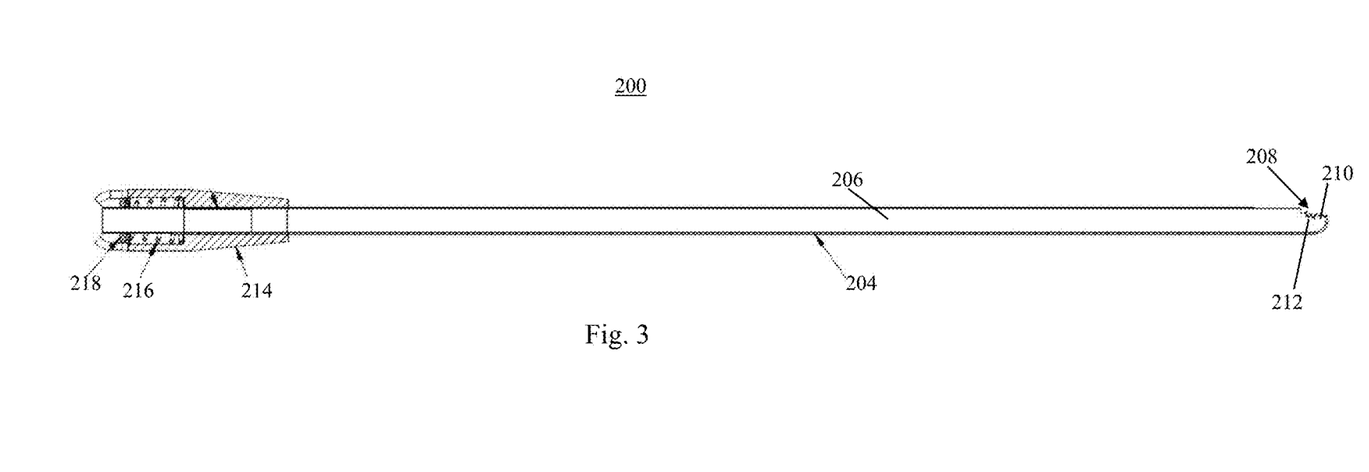
FIG. 3 is a cross sectional view of an inner shaft assembly.

With further reference to the cross section of FIG. 3, the inner shaft assembly 200 includes a first tubular member 204 defining a lumen 206 and a cutting tip 208. In one embodiment, the cutting tip 208 defines a serrated edge 210 including teeth surrounding an opening 212 that is fluidly connected to the lumen 206. Alternatively, the cutting tip 208 can assume a variety of other forms. In one embodiment, the first tubular member 204 is formed of a rigid material, such as 304 stainless steel, and is linear in longitudinal extension. Alternatively, the first tubular member 204 can be configured to effectuate bending thereof, such as by a flexible coupling (not shown). A hub 214 coupled to the first tubular member 204 is adapted for connection to the motor of the handpiece 130 (FIG. 1). The motor provides rotational power to the inner shaft assembly 200. The inner shaft assembly 200 further includes a biasing member 216 disposed within the hub 214. Upon final assembly, biasing member 216 biases the cutting tip 208 into contact with outer shaft assembly 202. A cap 218 retains the biasing member within the hub 214 and also creates a fluid seal to suction source 136. In one embodiment, lumen 206 is fluidly coupled with suction source 136 (FIG. 1) to provide aspiration of tissue that is cut by the cutting tip 208.

Figure 4:
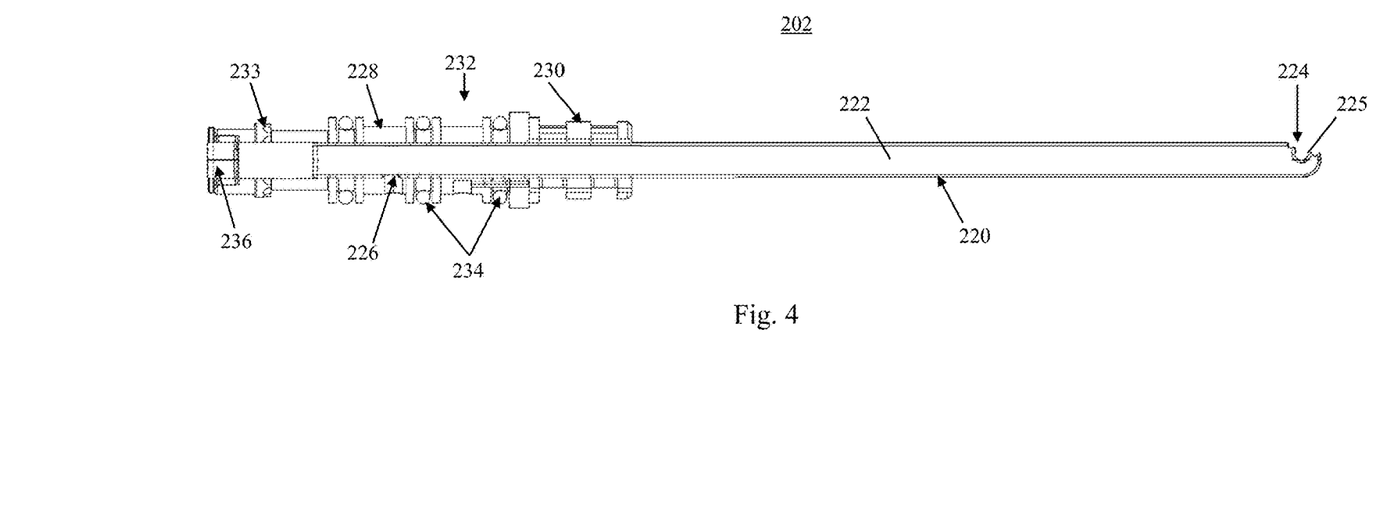
FIG. 4 is a cross section view of an outer shaft assembly.

As illustrated in the cross section of FIG. 4, the outer shaft assembly 202 includes a second tubular member 220 defining a lumen 222 and a cutting window 224. The cutting window 224, in one embodiment, is defined by a serrated edge 225. In one embodiment, the second tubular member 220 is rigid and longitudinally straight or linear and formed by 304 stainless steel. In alternative embodiments, the second tubular member 220 can incorporate, or be forced to assume, one or more bends. Regardless, the second tubular member 220, and in particular the lumen 222, is sized to co-axially receive the first tubular member 204 in a manner that allows rotation and/or oscillation of the first tubular member 204 relative to second tubular member 220, as well as to provide a path for internal irrigation. To this end, the lumen 222 of the second tubular member 220 has a diameter slightly greater than an outer diameter of a corresponding portion of the first tubular member 204, and defines an irrigation inlet 226 fluidly connected to the lumen 222.

A first, proximal hub member 228 and a second, distal hub member 230 form a hub assembly 232. The hub assembly 232, including the first hub member 228 and the second hub member 230, are connected to tubular member 220 in a fixed manner so as to rotate together. As such, rotation of the hub assembly 232 causes rotation of the cutting window 224. The hub assembly 232 is adapted for connection to the actuator 138 (FIG. 1) in order to rotate the outer shaft assembly 202, and thus the cutting window 224, relative to the housing 120 (FIG. 1) and the inner shaft assembly 200. In particular, the hub 228 can include an engagement member 233 (e.g., gear teeth) that directly couples with a drive member (e.g., a gear) of the actuator 138 to effectuate rotation of hub 228 and, due to the fixed coupling with hub assembly 232 and tubular member 220, the cutting window 224. A plurality of o-rings 234 are coupled to the first hub member 228 to provide seals for the first hub member 228, as discussed below. In addition, a cap 236 is provided at a proximal end of the outer shaft assembly 202.

Returning to FIGS. 2A and 2B, device 110 further includes wiring 240 electrically connected with power source 132 (FIG. 1). Wiring 240 extends to a button activation assembly 242 that includes button 122. Upon depressing the button 122, button activation assembly 242 controls flow of electrical energy between the wiring 240 and a printed circuit board (PCB) 244. The PCB 244 is coupled with first and second electrode assemblies 246 and 248. The electrode assemblies 246 and 248 are electrically isolated from one another so as to provide bipolar electrical energy delivery to tissue positioned proximate the distal region 114.

Figure 5:
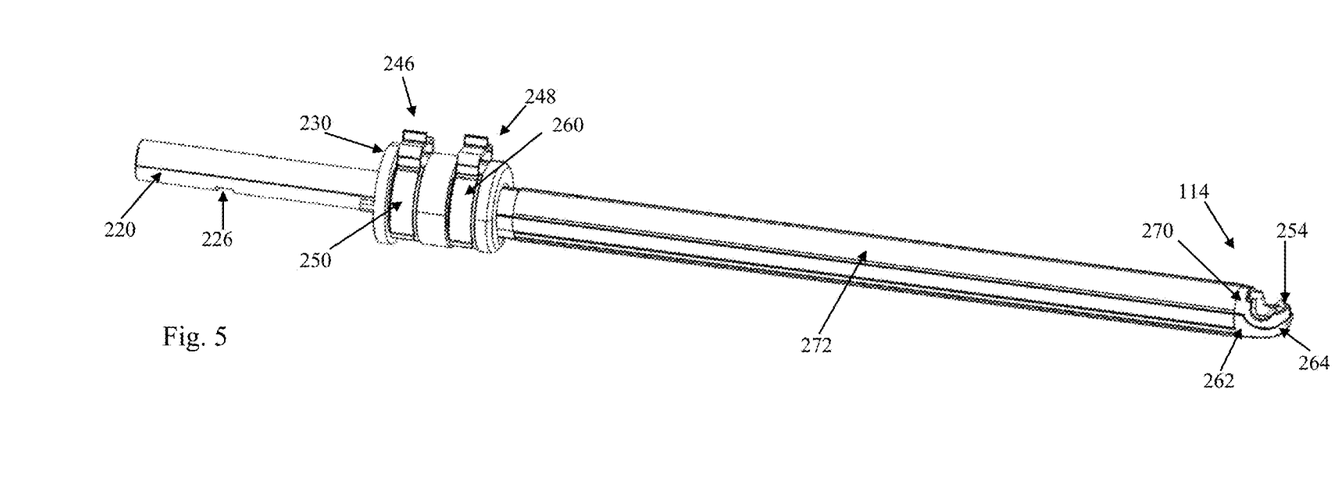
FIG. 5 is an isometric view of first and second electrode assemblies.

As illustrated in FIG. 5, the first electrode assembly 246 includes a first rotary electrical connection assembly 250 maintained by second hub member 230, second tubular member 220 (forming a first elongate electrode body) and a first electrode 254 positioned at distal end region 114 of the device 110. In a similar manner, the second electrode assembly 248 includes a second rotary electrical connection assembly 260 maintained by second hub member 230, a second elongate electrode body 262 and a second electrode 264 positioned at distal end region 114 of device 110. Electrodes 254 and 264 comprise bipolar electrodes and may comprise wet or dry electrodes. Electrodes 254 and 264 may be used to deliver any suitable energy for purposes of coagulation, hemostasis or sealing of tissue.

In one embodiment, the electrode 254 is formed by leaving a surface area of the tubular member 220 free of insulating material. In like manner, the electrode 264 can be formed by leaving a surface area of the electrode body 262 free of insulating material. For example, an insulating coating 270 is applied to second tubular member 220 to electrically isolate second tubular member 220 from electrode body 262. In addition, an insulating layer 272 (e.g., formed from through a heat shrinking process) can be applied around electrode body 262.

Figure 6:
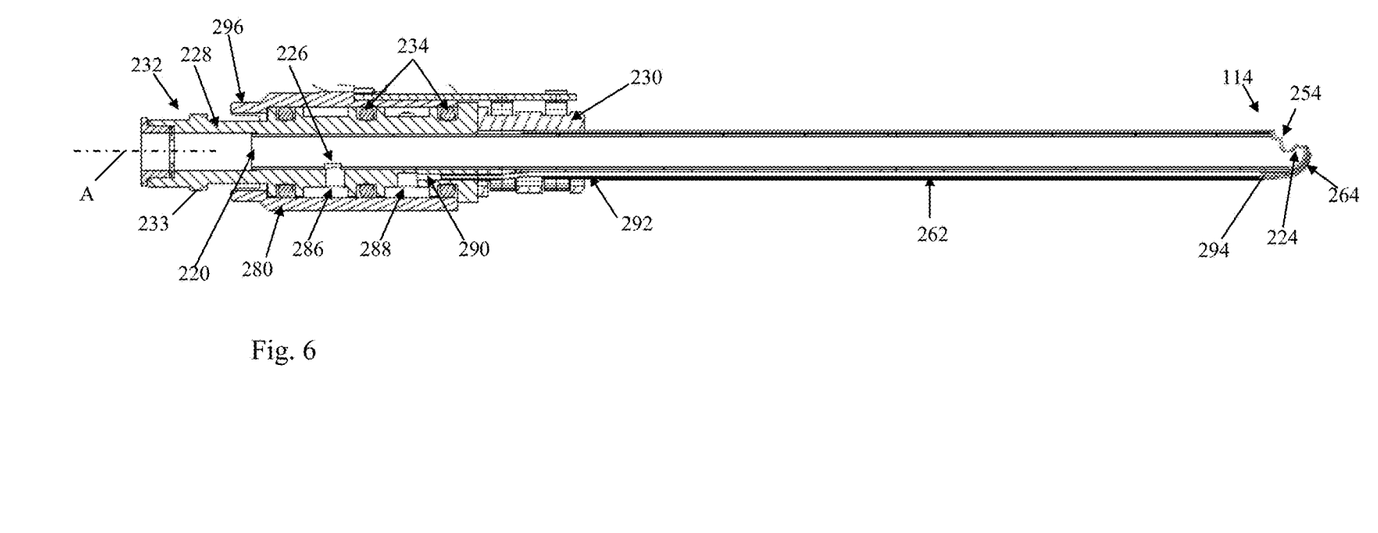
FIG. 6 is a cross section of an irrigation hub and associated irrigation paths.

With reference to FIGS. 2A, 2B and 6, electrodes 254 and 264 are particularly useful with fluid such as saline provided by fluid source 134 (FIG. 1) which may be carried along blade assembly 124 within an irrigation path and emitted at distal end region 114. In order to provide fluid delivery to distal end region 114, device 110 includes an irrigation hub 280. As illustrated in FIG. 2A, irrigation hub 280 includes a first fluid connector 282 and a second fluid connector 284.

First fluid connector 282 is fluidly coupled with a first annular channel 286 formed in first hub member 228. First annular channel 286 is fluidly coupled with irrigation inlet 226. Fluid entering inlet 226 is carried within lumen 222 between first tubular member 204 and second tubular member 220. Fluid carried within lumen 222 is dispensed through cutting window 224. As such, an irrigation path is established that includes channel 286, lumen 222 and an outlet at cutting window 224.

Second fluid connector 284 is fluidly coupled with a second annular channel 288 formed in first hub member 228. Second annular channel 288 is fluidly coupled with a passageway 290 disposed within the first hub member 228 and connected with tubing 292 positioned between second tubular member 220 and electrode body 262. Tubing 292 terminates at an end 294 proximal the electrodes 254 and 264. As such, an irrigation path is established that includes channel 288, passageway 290, tubing 292 and an outlet between electrodes 254 and 264.

Figure 7:
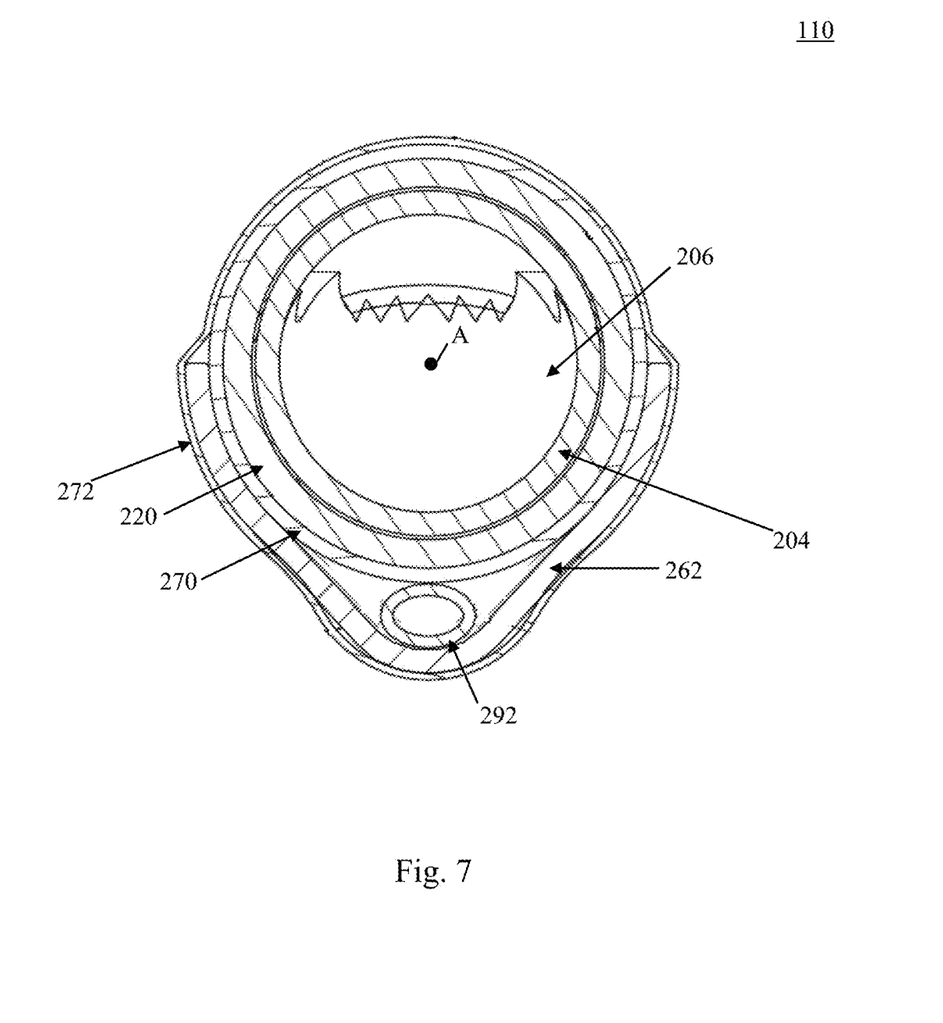
FIG. 7 is a cross section of the bipolar electrical device illustrated in FIG. 2A taken along line 7-7.

FIG. 7 illustrates a cross section of device 110 along line 7-7 in FIG. 2A, further illustrating the relationship among tubular member 204, tubular member 220, insulating layer 270, electrode body 262, tubing 292 and insulating layer 272. As illustrated, tubing 292 is elliptical in cross section, but can be formed of other cross sectional shapes as well (e.g., a circle). The electrode body 262 is U-shaped, adjoining with the insulating coating 270 on either side of the tubing 292.

During operation, and with reference to FIG. 1, device 110 is coupled to handpiece 130 by inserting the proximal end region 112 into an opening (not shown) in the handpiece 130. In particular, the hub 214 is inserted into the opening and can include a proximal engagement member 295 (e.g., including tabs illustrated in FIGS. 2A and 2B) for coupling with the motor of the handpiece 130. Upon insertion of the device 110 into the handpiece 130, actuator 138 engages with the engagement member 233 of hub 228. In one embodiment, the irrigation hub 280 (or other component of device 110) can include one or more alignment tabs 296 that orient the housing 120 with respect to the handpiece 130. In one particular embodiment, the tabs 296 are arranged such that coupling between device 110 and handpiece 130 orients button 122 perpendicular to a rotational axis of actuator 138. In the embodiment illustrated in FIG. 1, a right-handed user will have access to button 122 and actuator 138 through their right index finger. In similar manner, device 110 can be rotated 180 degrees prior to insertion into the handpiece 130 such that button 122 faces an opposite direction to that illustrated in FIG. 1. In this orientation, a left-handed user will have access to button 122 and actuator 138 through their left index finger. Upon final connection with the handpiece 130, device 110 may comprise two modes: a cutting or debridement mode and a sealing or hemostasis mode. These two modes may further be mutually exclusive. In an alternative embodiment, the two modes can be performed simultaneously.

As illustrated in FIGS. 8A and 8B, the cutting tip 208 provided by the first tubular member 204 is selectively exposed at the cutting window 224 relative to tissue site T. Upon final assembly, the cutting tip 208 is positioned at the cutting window 224 with the two components being rotatable relative to one another in oscillation or rotation (or both) in order to mechanically cut tissue (e.g., as driven by a motor contained within the handpiece 130 coupled with the power source 132 of FIG. 1). The cutting tip 208 and the cutting window 224 combine to define a cutting implement 300. Hemostasis is achieved via energy delivery to tissue T through energy delivered to electrodes 254 and 264. In one embodiment, one of the electrodes is an active electrode and one of the electrodes is a passive electrode. Alternatively, the electrodes are of alternating polarity and switch between sourcing and returning electrical current periodically. Regardless of the particular construction, electrical energy passes from the source electrode through tissue to the return electrode. Electrical energy delivered distal end region 114 passes from the active electrode, through tissue T and to the return electrode. In one embodiment, hemostasis is delivered while cutting implement 300 is not active or cutting. In one embodiment, energy may be advantageously delivered simultaneously with a fluid such as saline to achieve an optimal tissue effect by delivering controlled thermal energy to tissue.

By way of explanation, FIG. 8A illustrates the first tubular member 204 rotated to a position whereby the cutting tip 208 is exposed via the cutting window 224 and away from tissue site T. Upon partial rotation of the second tubular member 220 relative to the first tubular member 204 as illustrated in FIG. 8B, or vice-versa, less of the cutting tip 208 is exposed at the cutting window 224 and the orientation of the cutting window 224 approaches the tissue site T. In some positions, the second tubular member 220 and the electrode body are rotated such that the central lumen 206 of the first tubular member 204 is closed relative to the cutting window 224. Regardless, the second tubular member 220 and the electrode body 262 are rotatable with respect to the first tubular member 204 in either direction a full 360 degrees through operation of the actuator 138 (FIG. 1). As such, operation of the actuator 138 can rotate the second tubular member 220 and the electrode body 262 from FIG. 8B to the position of FIG. 8A in either direction as desired so as to face the tissue site T of interest.

Specific surgical techniques facilitated by the surgical cutting instruments described herein can be conducted in connection with features discussed above. During use, a hand (not shown) of a user (not shown) is employed to grasp the handpiece 130 (FIG. 1). In this regard, and in one embodiment, the handpiece 130 forms an exterior contour adapted to ergonomically fit within a user's hand, such as by grasping the handpiece 130. Regardless, the user then deploys the cutting implement 300, manipulating the handpiece 130 to deploy the cutting implement 300 to target site T. Following initial deployment to the target site T, the cutting window 224 has a first spatial orientation relative to the target site as indicated by the orientation of the cutting window 224 relative to target site T. More particularly, with the orientation of FIG. 8A, the cutting window 224 exposes the cutting tip 208. Further, the handpiece 130, can be generally described as defining an upright orientation as illustrated in FIG. 1 when naturally grasped by the user's hand, with the handpiece 130 positioned within the user's palm, such that the actuator 138 is proximate the user's thumb or index finger (not shown). In addition, the button 122 can be in close proximity to actuator 138 such that the user can easily switch back and forth by controlling spatial orientation of cutting window 224 and delivering RF energy through operation of button 122.

An example surgical procedure may then require removal of tissue and/or hemostasis of tissue T in a direction not directly facing or adjacent the cutting window 224. In the orientation of FIG. 8A, the cutting window 224 is away from the tissue site T, requiring movement of the cutting window 224 to allow either the cutting tip 208 or the electrodes 254 and 264 to interact with the tissue T. To accomplish alteration of the spatial orientation of the cutting window 224, and with additional reference to FIG. 8A, the user (not shown) rotates the actuator 138 in a desired direction. In particular, the user's thumb (not shown) and/or index finger (not shown) of the hand that is otherwise grasping the handpiece 130 is used to rotate the actuator 138. Rotation of the actuator 138 is translated to the hub 228. Rotation of the hub 228, in turn, causes the second tubular member 220, and thus the cutting window 224, to rotate relative to the tissue site T, the housing 120, the cutting tip 208 and the handpiece 130. Rotation of the actuator 138 continues until the cutting window 224 assumes the second spatial orientation shown in FIG. 8B. Notably, a rotational orientation of the handpiece 130, need not change when translating the cutting window 224 from the spatial orientation of FIG. 8A to the spatial orientation of FIG. 8B or any other orientation relative to axis A to face the tissue site T. That is to say, the cutting window 224 can be rotated to face any direction about axis A.

Transition of the cutting window 224 from the spatial orientation of FIG. 8A to the spatial orientation of FIG. 8B (or other orientation as desired throughout a full 360 degree rotation about axis A) is accomplished, in one embodiment, with only a single hand of the user. The device 110 is configured such that the cutting window 224 can be spatially rotated relative to the handpiece 130 without requiring both hands of the user to otherwise grasp the handpiece at two discrete locations and apply a twisting or torque-generating motion. In one embodiment, the single-handed cutting window rotation is accomplished by configuring the actuator 138 such that a movement axis of the actuator 138 is off-set from axis A, which is coaxial with a major axis of the hub 228. That is to say, the actuator 138 moves (e.g. rotates) about an axis or plane that is not co-axial with axis A of the hub 228; instead, movement of the actuator 138 is translated into rotation of the hub 228 about the axis A of the second hub 228. In one embodiment, the rotational axis of the actuator 138 is perpendicular to axis A. With this approach, then, the actuator 138 can be located at any desired position relative to the handpiece 130 so as to promote single-handed operation.

During delivery of electrical energy in hemostasis mode, fluid can be provided to distal end region 114 through cutting window 224, outlet 294 (FIG. 6), or both. Fluid delivered to distal end region 114 interacts with electrodes 254 and 264. In this manner, electrodes 254 and 264 can advantageously provide Transcollation® sealing of tissue when used with the Transcollation® sealing energy supplied by the Aquamantys System, available from the Advanced Energy Division of Medtronic, Inc. With respect to "wet" RF coagulation technology, the technology for sealing tissue described in U.S. Pat. Nos. 6,558,385; 6,702,810, 6,953,461; 7,115, 139, 7,311,708; 7,537,595; 7,645,277; 7,811,282; 7,998, 140; 8,048,070; 8,083,736; and 8,361,068 (the entire contents of each of which is incorporated by reference) describe bipolar coagulation systems believed suitable for use with device 110. Other systems for providing a source of energy are also contemplated.

Figure 9A:
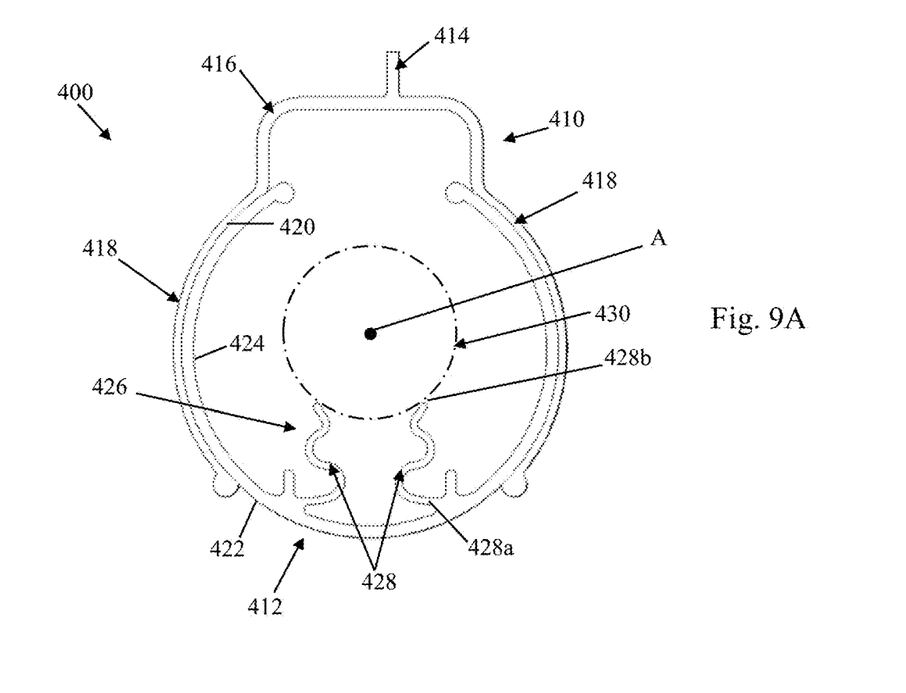
FIGS. 9A and 9B are plan views of first and second rotary electrical connection assemblies, respectively.
Figure 9B:
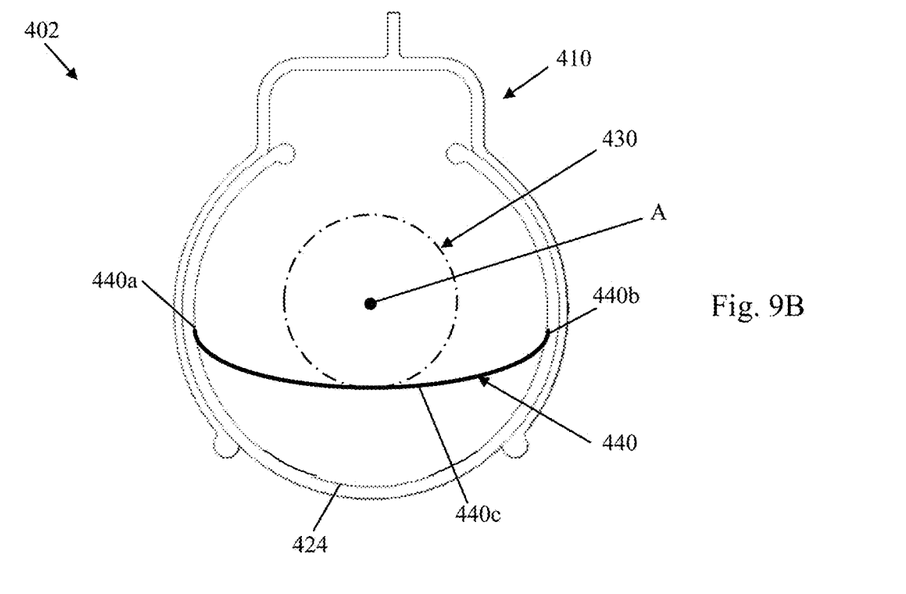

FIGS. 9A and 9B illustrate example rotary electrical connection assemblies 400 and 402, respectively, which allow device 110 to provide 360 degree rotation of the cutting window 224 with respect to housing 120 while still providing electrical energy to the distal region 114. Either of the assemblies 400, 402 can be used as the rotary electrical connection assemblies 250 and 260 discussed with respect to FIG. 5. With reference to assembly 400 illustrated in FIG. 9A, the assembly 400 includes an outer, stationary connector 410 and an inner, rotating connector 412. Each of the outer connector 410 and the inner connector 412 for a partial ring-like structure extending about rotational axis A at least 180 degrees, although other structures can be utilized. The inner connector 412 is connected to hub 230 to rotate therewith, while outer connector 410 is held stationary upon rotation of hub 230 about axis A. The outer connector 410 and the inner connector 412 can be formed of material exhibiting suitable electrical conductive properties, such as brass. The stationary connector 410, in one embodiment, is a unitary body that includes an extension 414, a bridge 416 coupled with the extension 414 and opposed arcuate arms 418 (e.g., arcuate segments) extending from opposite sides of the bridge 416. The extension 414 is configured to connect to the PCB 244 (FIG. 2). Electrical energy provided to the extension 414 is carried by the bridge 416 to each of the arms 418.

The arms 418 define an inner engagement surface 420 that is in contact with the inner connector 412, in particular an outer, first surface 422 of the inner connector 412. An inner, second surface 424 of the inner connector is opposite first surface 422. An inner extension member 426 extends inwardly toward axis A to connect with an arcuate connecting surface 430. In one example, arcuate surface 430 is second tubular member 220 or electrode body 262. Extension member 426 exhibits resilient properties and defines a natural position and a deflected position in order to engage and capture arcuate surface 430. In the illustrated embodiment, extension member 426 includes a pair of opposed tabs 428 extending from the second surface 424. Each tab 428 includes a first end 428a connected with the second surface 424 and a second end 428b opposite the first end 428a. Upon coupling of the member 426 with the arcuate surface 430, the second ends 428b of each of the tabs 428 deflect away from the rotational axis A. The resilient properties of the extension member 426 maintain contact with the arcuate surface 430 upon final assembly.

Assembly 402 illustrated in FIG. 9B is similar to assembly 400, with similar elements similarly numbered. In contrast to assembly 400 of FIG. 9A, assembly 402 includes an extension member 440 that extends from a first end 440a connected to inner surface 424 to a second end 440b that is connected to inner surface 424 at a different position. An intermediate portion 440c of the extension member 440 transitions from a natural position to a deflected position when coupled with arcuate surface 430. Due to resilient properties of extension member 440, the intermediate portion 440c maintains electrical contact with arcuate surface 430 upon final assembly.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An irrigated, bipolar electrosurgical device having a rotary electrical connection assembly, comprising:
    an outer connector defining an engagement surface;
    an inner connector rotatably disposed within the outer connector about a rotational axis, comprising:
        a first surface in contact with the engagement surface of the outer connector; and
        a second surface opposite the first surface; and
        an extension member extending from the second surface in a direction away from the first surface, the member defining a natural position and a deflected position; and
    an electrode defining an outer arcuate connecting surface positioned in contact with the extension member such that the extension member is in the deflected position;
    wherein the connecting surface is positioned at a proximal end of the electrode and wherein the electrode includes a distal end opposite the proximal end, the distal end defining an electrode surface configured to deliver electrical energy;
    and further wherein electrical energy provided to the outer connector is delivered to the electrode via the inner connector.

2. The connection assembly of claim 1, wherein the extension member includes a pair of opposed tabs, each tab includes a first end connected with the second surface and a second end opposite the first end, the second end rotating about the first end when the extension member transitions between the natural position and the deflected position.

3. The connection assembly of claim 2, wherein each second end deflects relative to the respective first end when in contact with the electrode.

4. The connection assembly of claim 1, wherein the extension member includes first and second ends connected to the second surface and an intermediate portion positioned between the first and second ends, wherein the intermediate portion deflects relative to the first and second ends when in contact with the electrode.

5. The connection assembly of claim 1, wherein the engagement surface is formed of opposed arcuate segments forming a partial ring-like structure.

6. The connection assembly of claim 1, wherein the first surface of the inner connector forms a partial ring-like structure.

7. The connection assembly of claim 1, wherein the engagement surface extends about the rotational axis at least 180 degrees.

8. The connection assembly of claim 1, wherein the first surface extends about the rotational axis at least 180 degrees.

9. The connection assembly of claim 1, wherein the distal end defines a cutting window.

10. The connection assembly of claim 1, wherein for a 360 degree rotation of the inner connector about the rotational axis, the second surface maintains contact with the engagement surface.

11. A bipolar electrical device having a proximal region and a distal region, the device comprising:
    a housing positioned at the proximal region;
    a first electrode assembly disposed within the housing, the first electrode assembly including a first stationary portion, a first rotating portion rotatably disposed within the first stationary portion and a first electrode coupled with the first rotating portion through a first extension member engaging a first outer arcuate connecting surface of the first electrode, wherein the first electrode defines a first electrode surface positioned at the distal region;
    a second electrode assembly disposed within the housing and electrically isolated from the first electrode assembly, the second electrode assembly including a second stationary portion, a second rotating portion rotatably disposed within the second stationary portion and a second electrode coupled with the second rotating portion through a second extension member engaging a second outer arcuate connecting surface, wherein the second electrode defines a second electrode surface positioned at the distal region;
    a hub rotatably disposed within the housing and connected with the first electrode assembly and the second electrode assembly, wherein upon rotation of the hub relative to the housing, the first rotating portion, the first electrode, the second rotating portion and the second electrode rotate with respect to the first stationary portion and the second stationary portion; and an irrigation path fluidly coupled with the hub and configured to deliver fluid from the proximal region to the distal region.

12. The bipolar electrical device of claim 11, wherein the first electrode is connected in fixed relation with the hub such that rotation of the hub about the rotation axis relative to the housing causes rotation of the first electrode relative to the housing.

13. The bipolar electrical device of claim 11, wherein the irrigation path is connected in fixed relation with the hub such that rotation of the hub about the rotation axis relative to the housing causes rotation of the irrigation path relative to the housing.

14. The bipolar electrical device of claim 11, wherein the device establishes an electrical current flow path along the first electrode assembly from the first stationary portion to the first rotating portion, then from the first extension member of the first rotating portion to the first outer arcuate connecting surface of the first electrode, and then from the first outer arcuate connecting surface to the first electrode surface.

15. A bipolar electrical device, comprising:
a proximal region maintaining a housing having a first electrical connection and a second electrical connection electrically isolated from the first electrical connection, the first and second electrical connections disposed within the housing and selectively electrically connected to wiring disposed within the housing;
a distal region opposite the housing;
an outer shaft rotatably disposed within the housing, the outer shaft defining a lumen, an outer circumference, a proximal end and a distal end opposite the proximal end, wherein the proximal end defines a first connection surface electrically connected with the first electrical connection and the distal end defines an outer shaft cutter defining a window in the outer shaft and a first electrode surface;
an inner shaft rotatably disposed within the lumen of the outer shaft, the inner shaft defining a distal portion opposite the proximal region, the distal portion further including an inner shaft cutter defining a cutting window in the inner shaft;
an electrode body rotatably disposed within the housing, extending along the outer circumference of the outer shaft to the distal region and electrically isolated from the outer shaft, the electrode body defining a second connection surface electrically connected with the second electrical connection and a second electrode surface spaced apart from the first electrode surface;
a hub rotatably disposed within the housing to support the outer shaft and the electrode body for rotation about a rotation axis, wherein upon rotation of the hub 360 degrees about the rotational axis, the outer shaft and the electrode body rotate relative to the housing and relative to the wiring, the first connecting surface maintains electrical connection with the first electrical connection and the second connecting surface maintains electrical connection with the second electrical connection; and
an irrigation path fluidly coupled with the hub and configured to deliver fluid from the proximal region to the distal region.

16. The bipolar electrical device of claim 15, wherein the electrode body is connected in fixed relation with the hub such that rotation of the hub about the rotation axis relative to the housing causes rotation of the electrode body relative to the housing.

17. The bipolar electrical device of claim 15, wherein the irrigation path is connected in fixed relation with the hub such that rotation of the hub about the rotation axis relative to the housing causes rotation of the irrigation path relative to the housing.

18. The bipolar electrical device of claim 15, wherein the first electrical connection includes a rotating portion rotatably disposed within a stationary portion, and further wherein the rotating portion includes an extension member in electrical contact with and extending away from the first connection surface of the outer shaft, and even further wherein an electrical current flow path is established from the stationary portion to the rotating portion, from the extension member of the rotating portion to the first connection surface, and from the first connection surface to the first electrode surface, and even further wherein the stationary portion is uncoupled from the hub such that with rotation of the hub, the rotating portion rotates and the stationary portion remains stationary.

19. The bipolar electrical device of claim 18, wherein the irrigation path is defined by a tube coupled to the hub, the tube being separate from the outer shaft and the inner shaft, and further wherein tube rotates with rotation of the hub.

20. A surgical system comprising:
a blade assembly, comprising:
a proximal region maintaining a housing having a first electrical connection and a second electrical connection electrically isolated from the first electrical connection, the first and second electrical connections disposed within the housing and selectively electrically connected to wiring disposed within the housing;
a distal region opposite the housing;
an outer shaft rotatably disposed within the housing, the outer shaft defining a lumen, an outer circumference, a proximal end and a distal end opposite the proximal end, wherein the proximal end defines a first connection surface electrically connected with the first electrical connection and the distal end defines an outer shaft cutter defining a window in the outer shaft and a first electrode surface;
an inner shaft rotatably disposed within the lumen of the outer shaft, the inner shaft defining a distal portion opposite the proximal region, the distal portion further including an inner shaft cutter defining a cutting window in the inner shaft;
an electrode body rotatably disposed within the housing, extending along the outer circumference of the outer shaft to the distal region and electrically isolated from the outer shaft, the electrode body defining a second connection surface electrically connected with the second electrical connection and a second electrode surface spaced apart from the first electrode surface;
a hub rotatably disposed within the housing to support the outer shaft and the electrode body for rotation about a rotation axis;
an irrigation path fluidly coupled with the hub and configured to deliver fluid from the proximal region to the distal region;
a handpiece coupled with the blade assembly, comprising:
an actuator assembly coupling the hub to the handpiece, the actuator assembly including an actuator rotatably mounted to the handpiece such that a portion of the actuator is exteriorly exposed for manual interface by a user;

wherein the actuator causes rotation of the window and the hub relative to the housing such that, upon rotation of the hub 360 degrees about the rotational axis, the outer shaft and the electrode body rotate relative to the housing and relative to the wiring, the first connecting surface maintains electrical connection with the first electrical connection and the second connecting surface maintains electrical connection with the second electrical connection.

21. The system of claim 20, wherein the blade assembly further includes a button activation assembly coupled to the housing for providing electrical communication between a source of energy through each of the first and second electrical contacts to the first and second electrode surfaces, the button activation assembly including a button exteriorly exposed for manual interface by a user, further wherein the actuator is rotatable relative to an actuator axis perpendicular to the rotational axis, and further wherein connection between the hub and the electrode body includes first and second orientations of the button relative to the handpiece, each orientation separated by 180 degrees relative to the rotational axis and extending perpendicular to the actuator axis.

22. The system of claim 20, wherein the electrode body is connected in fixed relation with the hub such that rotation of the hub about the rotation axis relative to the housing causes rotation of the electrode body relative to the housing.

23. The system of claim 20, wherein the irrigation path is connected in fixed relation with the hub such that rotation of the hub about the rotation axis relative to the housing causes rotation of the irrigation path relative to the housing.

* * * * *